United States Patent [19]

Norris et al.

[11] Patent Number: 5,013,539

[45] Date of Patent: May 7, 1991

[54] METHOD AND COMPOSITION FOR ANTAGONISM OF SODIUM NITROPRUSSIDE TOXIC EFFECTS

[76] Inventors: James C. Norris, c/o Technical Laboratory Weyerhauser Co.; P.O. Box 188, Longview, Wash. 98632; Arthur S. Hume, 6247 Mossline Dr., Jackson, Miss. 39211

[21] Appl. No.: 835,991

[22] Filed: Mar. 4, 1986

[51] Int. Cl.$^5$ .............................................. A61K 00/00
[52] U.S. Cl. ..................................... 424/10; 514/922; 514/502
[58] Field of Search .......................... 424/10, 162, 164; 514/922, 502, 574

[56] References Cited

U.S. PATENT DOCUMENTS 3,542,929 11/1970 Roberts .............................. 514/561
4,256,731 3/1981 Curtis et al. ......................... 424/54

OTHER PUBLICATIONS

Norris et al., "Antagonism of Sodium Nitroprusside Induced Lethality by α-Ketoglutaric Acid", Federation Proceedings, vol. 44, 3, 1799, 1985.

Moore et al., "The Efficacy of α-Ketoglutaric Acid in the Antagonism of Cyanide Intoxication", Federation Proceedings, vol. 44, 3, 1800, 1985.

Primary Examiner—Douglas W. Robinson
Assistant Examiner—R. Kearse
Attorney, Agent, or Firm—George L. Williamson

[57] ABSTRACT

The present invention improves the safety of the use of sodium nitroprusside in the clinical setting. Specifically, this invention utilizes α-ketoglutaric acid or α-ketoglutaric acid and sodium thiosulfate to reduce sodium nitroprusside's toxic effects.

19 Claims, 2 Drawing Sheets

METHOD AND COMPOSITION FOR ANTAGONISM OF SODIUM NITROPRUSSIDE TOXIC EFFECTS

This invention was made with Government support under contract DAMD17-85-C-5286 awarded by the U.S. Army. The Government has certain rights in this invention.

BACKGROUND OF THE INVENTION

1. Field of Invention

The present invention improves the safety of the use of sodium nitroprusside in the clinical setting. Specifically, this invention suggests that alpha-ketoglutaric acid or alpha-ketoglutaric acid and sodium thiosulfate antagonize sodium nitroprusside's toxic effects. The antagonism of sodium nitroprusside's toxic effects by alpha-ketoglutaric acid or alpha-ketoglutaric acid and sodium thiosulfate is effective as a prophylactic treatment administered prior to exposure to sodium nitroprusside as a simultaneous treatment administered with exposure to sodium nitroprusside, and as an antidotal treatment administered following exposure to sodium nitroprusside. Alpha-ketoglutaric acid or alpha-ketoglutaric acid and sodium thiosulfate provide better antagonism of sodium nitroprusside's toxic effects than other regimens utilized in the past. The presence of alpha-ketoglutaric acid or sodium thiosulfate does not prevent the hypotension induced by sodium nitroprusside. This hypotension is the desirable effect of sodium nitroprusside. Alpha-ketoglutaric acid and sodium thiosulfate are without toxicological properties.

2. Prior Art

In the metabolism of nitroprusside (or sodium nitroprusside or other salts of nitroprusside) in a mammalian system cyanide is produced and released in the body. Thus, the primary toxicity of sodium nitroprusside is that of cyanide. Presently an individual exposed to a toxicological dose of sodium nitroprusside is administered sodium thiosulfate. Sodium thiosulfate protects against sodium nitroprusside's toxic effects indirectly by antagonizing the toxic effects of the cyanide released from the sodium nitroprusside. Cyanide is detoxified by an enzyme, rhodanese, which primarily resides in the liver. The substrate for rhodanese, sulpbate, is the limiting factor in protection against sodium nitroprusside's toxic effects. Administration of sodium thiosulfate provides additional substrate for rhodanese and thus enhances the body's ability to detoxify cyanide. Sodium thiosulfate must circulate to the liver before it can provide any assistance in cyanide detoxification. Consequently, there is a delay from the time of sodium thiosulfate administration to time of affecting the detoxification of cyanide.

Direct binding of cyanide by other chemicals have been proposed. Cobalt edetate is a chemical that binds cyanide but it has toxic effects of its own, e.g. atrial fibrillation, gastrointestinal hemmorrhage and anaphylactoid reactions. Another chemical that binds cyanide is hydroxocobalamin. Since one molecule of hydroxocobalamin binds one molecule of cyanide, large quantities would be needed to bind all the cyanide released from sodium nitroprusside. Experimental data suggest that the weight of hydroxocobalamin used would have to be 250 times the weight of sodium nitroprusside.

Listed below are selected articles known to the inventors on sodium nitroprusside's toxic effects and antagonism of sodium nitroprusside's toxic effects.

Arnold, W. P., Longnecker, D. E., and Epstein, R. M. (1984). Photodegradation of sodium nitroprusside: Biologic activity and cyanide release. Anesthesiology, 61: 254.

Bulter, A. R., Glidewell, C., and Bisset, W. I. K. (1982). Sodium nitroprusside and cyanide release. Br. J. Anaesth. 54: 792.

Davies, D. W., Kadar, D., Steward, D. J., and Munro, I. R. (1975). A sudden death associated with the use of sodium nitroprusside for induction of hypotension during anaesthesia. Canad. Anaesth. Soc. J. 22: 547.

Graham, G. G., and Rigg, D. (1983). Nitroprusside infusions. Br J. Anaesth. 55: 919.

Isom, G. E., Burrows, G. E., and Way, J. L. (1982). Effect of oxygen on the antagonism of cyanide intoxication-cytochrome oxidase, in vivo. Toxicol. Appl. Pharmacol. 65: 250.

Jack, R. D. (1974). Toxicity of sodium nitroprusside. Br. J. Anaesth. 46: 952.

Keilin, D. (1929). Cytochrome and respiratory enzymes. Proc. Roy. Soc. Ser. B. 104: 206.

Merrifield, A. J., and Blundell, M. D. (1974). Toxicity of sodium nitroprusside. Br. J. Anaesth. 46: 324.

Moore, S. J., Norris, J. C., Ho, I. K., and Hume, A. S. (1986). The efficacy of $\alpha$-ketoglutaric acid in the antagonism of cyanide intoxication. Tox. Appl. Pharmacol. 82: 40.

Norris, J. C., and Hume, A. S. (1985). Antagonism of sodium nitroprusside-induced lethality by $\alpha$-ketoglutaric acid. Federation Proceedings 44: 719.

Norris, J. C., and Hume, A. S. (1986). In vivo release of cyanide from sodium nitroprusside. Br. J. Anaesth. (In Press).

Smith, F. M., Aitken, D. M., West, D. W., Peterson, E. W., and Posnanski, W. D. (1977). Cyanide toxicity associated with sodium nitroprusside use. Ann. R. Coll. Phys. Surg. Can. 10: 83.

Smith, R. P., Kruszyna, H., and Kruszyna, R. (1982). Cyanide release from nitroprusside. Br. J. Anaesth. 54: 1145.

Vesey, C. J., Cole, P. V., Linnell, J. C., and Wilson, J. (1974). Some metabolic effects of sodium nitroprusside in man. Br. Med. J. 2: 140.

Vesey, C. J., Cole, P., and Simpson, P. (1976). Changes in cyanide concentrations induced by sodium nitroprusside. Br. J. Anaesth. 48: 268.

Vesey, C. J., and Batistoni, G. A. (1977). The determination and stability of sodium nitroprusside in aqueous solution. J. Clin. Pharm. 2: 105.

Vesey, C. J., Cole, P., and Simpson, P. (1982). Sodium nitroprusside and cyanide release. Br. J. Anaesth. 54: 791.

3. Summary Discussion of the Invention

It is an object of the present invention to provide an antagonist to sodium nitroprusside's toxic effects which is fast acting and is free from its own toxic properties.

It is another object of the present invention to provide an antagonist to sodium nitroprusside's toxic effects which is effective as a preventive measure administered prior to and simultaneous with exposure to sodium nitroprusside and as a remedial measure employed after exposure to sodium nitroprusside.

It is still another object of the present invention to provide an antagonist to sodium nitroprusside's toxic effects which may be employed singularly or in concert with presently known antagonists to sodium nitroprusside's toxic effects, e.g., sodium thiosulfate, for an additive effect.

DETAILED DESCRIPTION OF THE PREFERRED EXEMPLARY EMBODIMENT(S)

Figure 1:
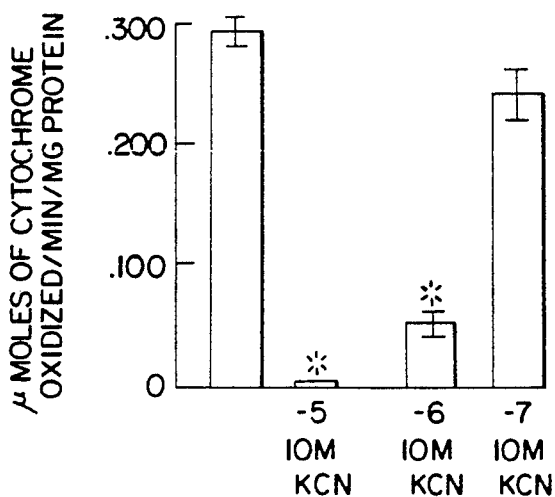

The present invention employs the use of the innocuous agent, alpha-ketoglutaric acid, in the treatment of sodium nitroprusside's toxic effects. Sodium nitroprusside releases cyanide ions in the body. The mechanism of action of alpha-ketoglutaric acid has been suggested to be due to cyanide binding to a significant extent to alpha-ketoglutaric acid. Thus, cyanide-induced inhibition of cytochrome oxidase activity is prevented. Inhibition of cytochrome oxidase activity is proposed to be the mechanism of cyanide's action.

The regimen of the present invention appears to be very efficacious in the protection of a laboratory mouse against cyanide's and sodium nitroprusside's toxic effect. Data obtained from laboratory mice demonstrate that alpha-ketoglutaric acid's antagonism of cyanide's toxic effect is greatly enhanced by additionally administering sodium thiosulfate fifteen minutes prior to cyanide administration.

The efficacy of the regimen of the present invention was determined by experimentation:

Potassium cyanide (KCN) and sodium nitroprusside (SNP) were the toxic agents. Alpha-ketoglutaric acid and sodium thiosulfate were used to antagonize these toxic agents. All solutions were prepared freshly in physiological saline (0.9% NaCl) on the day of experimentation. Alpha-ketoglutaric acid was dissolved in saline and the solution was adjusted to pH 7.4 with sodium hydroxide.

Male ICR mice weighing 23 to 28 g were used in this section. Mice were given food and water ad libitum and were housed in a temperature-controlled environment with a photo-period of 12 hours light/12 hours dark. Each experimental group was selected randomly from the general mouse population.

Pretreatment protocol was as follows: Sodium thiosulfate (1 g/kg, inter-peritoneally, hereinafter "i.p.") was injected 15 minutes before cyanide administration. A dose of 2 g/kg, i.p., of α-ketoglutaric acid was injected 10 minutes prior to the cyanide injection. No lethality was observed in the animals as the result of the administration of α-ketoglutaric acid in doses of 1, 2, and 4 grams per kilogram of body weight. Volumes of the injected solutions were kept small (0.1 ml/10 g of body weight) and the cyanide was always injected antipodal to the peritoneal region into which the cyanide antagonists were injected, in order to decrease any likelihood of intraperitoneal binding between cyanide and the cyanide antagonists. Varying doses of cyanide were administered (10 animals per dose) in order to generate a lethality curve. The particular drugs and drug combinations utilized are delineated in Table 1. $LD_{50}$ values for cyanide were determined 12 hours after cyanide injection.

TABLE 1

Effects of Pretreatment Regimen on the $LD_{50}$ Value of Potassium Cyanide in Mice

| Pretreatment Regimen | $LD_{50}$ Value (mg/kg, i.p.) | % of Control $LD_{50}$ Value |
| --- | --- | --- |
| Controls | 6.5 (6.3–6.6) | 100.0 |
| Sodium thiosulfate | 17.0 (14.7–19.6) | 263.6 |
| Alpha-ketoglutaric acid | 32.0 (28.1–36.5) | 496.1 |
| Alpha-ketoglutaric acid + Sodium thiosulfate | 105.0 (100.0–110.3) | 1627.9 |

Table 1 details the effect of each treatment protocol upon the $LD_{50}$ value of KCN in mice administered with various concentrations to cyanide. It highlights the remarkable efficacy of alpha-ketoglutaric acid given alone, and in combination with sodium thiosulfate. These data illustrate the superior efficacy of alpha-ketoglutaric acid over sodium thiosulfate. However, the combination of alpha-ketoglutaric acid and sodium thiosulfate provides a dramatic protection against KCN-induced lethality.

TABLE 2

Comparison of the Effects of α-Ketoglutaric Acid on Pretreatment Regimen

| Group | Pretreatment Regimen | *Potency Ratio |
| --- | --- | --- |
| A. | Control | 5.0 (4.5–5.5) |
| B. | Alpha-ketoglutaric acid | |
| A. | Sodium thiosulfate | |
| B. | Sodium thiosulfate + Alpha-ketoglutaric acid | 6.2 (5.4–7.1) |

*Potency ratio = $\frac{LD_{50} \text{ Value of KCN in Group B}}{LD_{50} \text{ Value of KCN in Group A}}$ Table 2 represents a comparison on the relative potency between two similar regimens, differing only by the addition of the alpha-ketoglutaric acid to the protocol, in terms of potency ratio. The potency ratio defined as $LD_{50}$ value of potassium cyanide (KCN) on animals are pretreated with sodium thiosulfate plus alpha-ketoglutaric acid or alpha-ketoglutaric acid alone over the $LD_{50}$ value of KCN of animals pretreated with sodium thiosulfate or saline alone (Control). The potency ratio of alpha-ketoglutaric acid vs. control was calculated to be a five fold increase. The potency ratio of sodium thiosulfate plus alpha-ketoglutaric acid pretreatment versus that of sodium thiosulfate alone was determined to be approximately six times (5.37–7.10) as great, another large augmentation in protective ability.

Data have also been obtained that demonstrate that alpha-ketoglutaric acid can effectively antidote cyanide-induced lethality (Table 3).

TABLE 3

Effects of Alpha-Ketoglutaric Acid Administered After Potassium Cyanide (KCN) Administration

| Time of Alpha-Ketoglutaric Acid Administration (sec) | Percentage Dead |
| --- | --- |
| 15 | 10* |

TABLE 3-continued

| Effects of Alpha-Ketoglutaric Acid Administered After Potassium Cyanide (KCN) Administration | |
| --- | --- |
| Time of Alpha-Ketoglutaric Acid Administration (sec) | Percentage Dead |
| 25 | 0* |
| 55 | 10* |

Animals were treated with alpha-ketoglutaric acid, 15, 25, and 55 sec after a KCN injection. The KCN dose administered to control animals resulted in 80% dead. Asterisks (*) indicate a statistical difference from control value (P<0.05).

The following data established the mechanism of sodium nitroprusside's toxic effect and evaluated the efficacy of alpha-ketoglutaric acid to antagonize sodium nitroprusside's toxic effect. In vitro inhibition of brain cytochrome oxydase activity by potassium cyanide (KCN) was performed to establish the sensitivity of the assay to the presence of cyanide. The results are illustrated in FIG. 1. These data show that there was complete inhibition of brain cytochrome oxidase activity with $10^{-5}$M KCN, 83% inhibition with $10^{-6}$M KCN, and no inhibition with $10^{-7}$M KCN.

FIG. 1 shows brain cytochrome oxidase activity after the in vitro addition of potassium cyanide (KCN). Asterisks (*) indicate a statistical difference from control values (P<0.05). The bars represent mean±s.e.m. of n=4.

Figure 2:
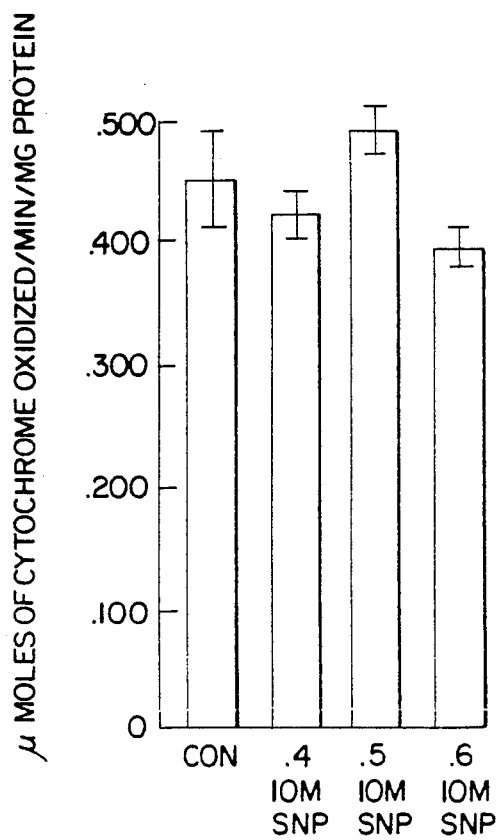

The effect of sodium nitroprusside (SNP) on brain cytochrome oxidase activity was determined (FIG. 2). These data demonstrate that the in vitro addition of SNP resulted in no inhibition of BCYTOX activity in the concentration range of $10^{-4}$M–$10^{-6}$M.

FIG. 2 shows cytochrome oxidase activity after the in vitro addition of sodium nitroprusside (SNP). The bars represent mean±s.e.m. of n=4.

Figure 3:
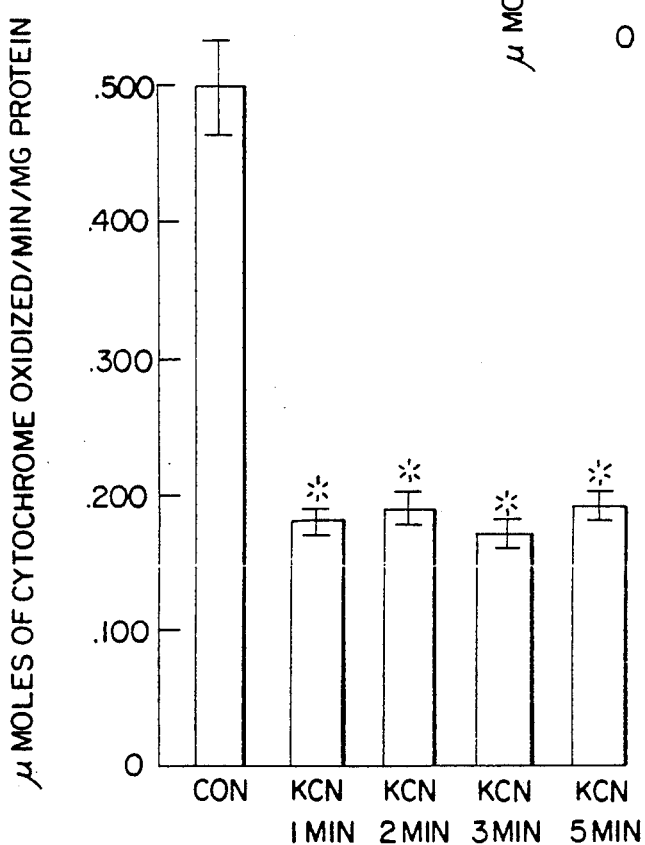

In vivo inhibition of brain cytochrome oxidase activity after administration of an $LD_{80}$ dose of KCN is illustrated in FIG. 3. This time course of enzymatic inhibition shows that one min after the injection of KCN there was a 60% inhibition of brain cytochrome oxidase activity. The inhibition continued to remain at that level for the other time points that brain cytochrome oxidase activity was measured.

FIG. 3 shows of an $LD_{80}$ dose of potassium cyanide (KCN) on brain cytochrome oxidase activity. Asterisks (*) indicate a statistical difference from control values (P<0.05). The bars represent mean±s.e.m. of n=4.

Figure 4:
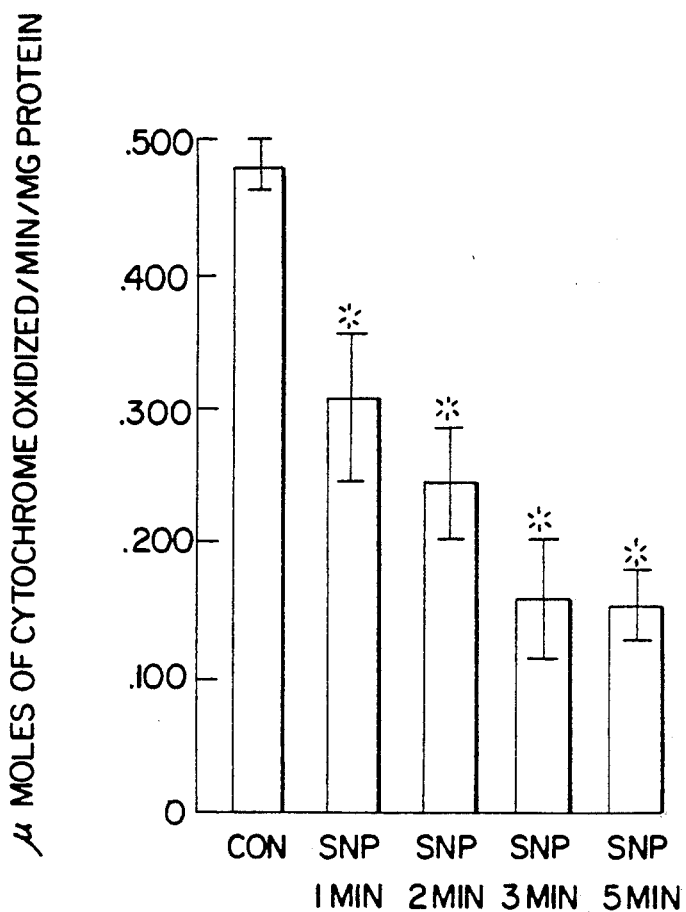

Data for the time course inhibition of brain cytochrome oxidase activity in animals administered an $LD_{80}$ dose of SNP are illustrated in FIG. 4. One min after the SNP injection there was inhibition of brain cytochrome oxidase activity, however, it was only 37% of control activity. At the two min time point the inhibition was 49% of control activity. It was not until the three min time point that the enzymatic inhibition was 60% of control activity.

FIG. 4 shows of an $LD_{80}$ dose of sodium nitroprusside (SNP) on brain cytochrome oxidase. Asterisks (*) indicate a statistical difference from control values (P<0.05). There was no statistical difference between brain cytochrome oxidase activities of SNP-treated animals. The bars represent mean±s.e.m. of n=4.

Figure 5:
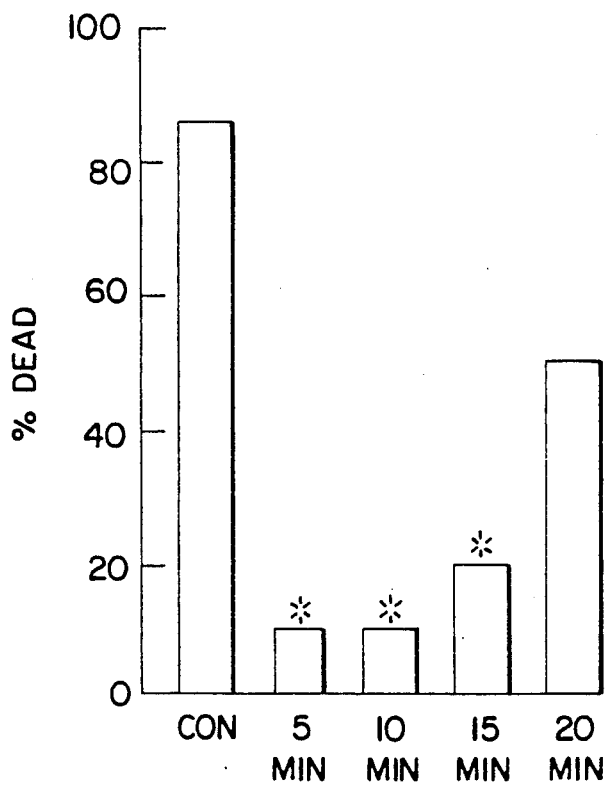

Different times of pretreatment with alpha-ketoglutaric acid and their antagonism of sodium nitroprusside-induced lethality are illustrated in FIG. 5. These data demonstrate that animals administered 2 g alpha-ketoglutaric acid/kg, 5, 10, and 15 minutes prior to $LD_{85}$ dose of sodium nitroprusside were significantly protected from sodium nitroprusside-induced lethality.

FIG. 5 shows of different pretreatment times of alpha-ketoglutaric acid on sodium nitroprusside-induced lethality. Asterisks (*) indicate a statistical difference from control values (P<0.05).

Induction of hypotension is the desired effect of sodium nitroprusside infusion. The addition of alpha-ketoglutaric acid to sodium nitroprusside does not abate the hypotension induced by sodium nitroprusside as monitored in rats. An infusion of 14 mg sodium nitroprusside/kg for thirty minutes resulted in 70% mortality. Several observations were noted in these animals: (1) bradycardia, (2) cardiac irregularities, (3) post-infusion hypotension and (4) death. Infusion of 14 mg sodium nitroprusside/kg mixed with alpha-ketoglutaric acid apparently eliminated these effects of sodium nitroprusside infusion.

Alpha-ketoglutaric acid has the benefit of being endogenously generated compound with relatively low toxicity and of being a relatively inexpensive compound. Further, animals treated with doses up to 2 g/kg of alpha-ketoglutaric acid showed no symptoms more remarkable than lethargy.

Pharmacological effective amount for humans are from about 0.1 g/kg of body weight to about 2.0 g/kg of body weight alpha-ketoglutaric acid.

When in combination with other pharmaceutical composition(s) the effective amounts of alpha-ketoglutaric acid are from about 0.1 g/kg of body weight to about 2.0 g/kg of body weight from about 0.1 g/kg of body weight to about 2.0 g/kg of body weight when used with from about 10 g total dose sodium thiosulfate.

Because many varying and different embodiments may be made within the scope of the inventive concept herein taught, and because many modifications may be made in the embodiment(s) herein detailed in accordance with the descriptive requirements of the law, it is to be understood that the details herein are to be interpreted as illustrative and not in a limiting sense.

What is claimed is:

1. A method for reducing sodium nitroprusside-induced toxic effects which comprises administering by infusion or injection a therapeutically effective amount of alpha-ketoglutaric acid to a person in need thereof prior to the administration of sodium nitroprusside.

2. A method for reducing sodium nitroprusside-induced toxic effects which comprises administering by infusion or injection a therapeutically effective amount of alpha-ketoglutaric acid to a person in need thereof during the administration of sodium nitroprusside.

3. A method for reducing sodium nitroprusside-induced toxic effects which comprises administering by infusion or injection a therapeutically effective amount of alpha-ketoglutaric acid to a person in need thereof following the administration of sodium nitroprusside.

4. A method for reducing sodium nitroprusside-induced toxic effects which comprises administering by infusion or injection a therapeutically effective amount of alpha-ketoglutaric acid and a therapeutically effective amount of sodium thiosulfate to person in need thereof prior to the administration of sodium nitroprusside, wherein said amount of alpha-ketoglutaric acid is from about 0.1 g/kg to about 2.0 g/kg of body weight and said amount of sodium thiosulfate is from about 1 g. to about 10 g. total dose.

5. The method of claim 4, which comprises administering said alpha-ketoglutaric acid and said sodium thiosulfate to said person during the administration of sodium nitroprusside.

6. The method of claim 4, which comprises administering said alpha-ketoglutaric acid and said sodium thiosulfate to said person following the administration of sodium nitroprusside.

7. The method of claim 1, which comprises administering from about 0.1 g/kg to about 2.0 g/kg of body weight of alpha-ketoglutaric acid to said person.

8. The method of claim 2, which comprises administering from about 0.1 g/kg to about 2.0 g/kg of body weight of alpha-ketoglutaric acid to said person.

9. The method of claim 3, which comprises administering from about 0.1 g/kg to about 2.0 g/kg of body weight of alpha-ketoglutaric acid to said person.

10. A method of enhancing a persons resistance to sodium nitroprusside-induced toxic effects which comprises administering by infusion or injection to a person in need thereof a therapeutically effective amount of alpha-ketoglutaric acid.

11. The method of claim 10, which comprises administering said alpha-ketoglutaric acid prior to the administration of said sodium nitroprusside.

12. The method of claim 10, which comprises administering said alpha-ketoglutaric acid during the administration of said sodium nitroprusside.

13. The method of claim 10, which comprises administering said alpha-ketoglutaric acid following the administration of said sodium nitroprusside.

14. A method of enhancing a persons resistance to sodium nitroprusside-induced toxic effects which comprises administering by infusion or injection a therapeutically effective amount of alpha-ketoglutaric acid and a therapeutically effective amount of sodium thiosulfate to a person in need thereof, wherein the amount of alpha-ketoglutaric acid is from about 0.1 g/kg to about 2.0 g/kg of body weight and the amount of sodium thiosulfate is from about 1 g. to about 10 g. total dose.

15. The method of claim 14, which comprises administering said alpha-ketoglutaric acid and said sodium thiosulfate prior to the administration of said sodium nitroprusside.

16. The method of claim 14, which comprises administering said alpha-ketoglutaric acid and said sodium thiosulfate during the administration of said sodium nitroprusside.

17. The method of claim 14, which comprises administering said alpha-ketoglutaric acid and said sodium thiosulfate following the administration of said sodium nitroprusside.

18. The method of claim 10, which comprises administering from about 0.1 g/kg to about 2.0 g/kg of body weight of alpha-ketoglutaric acid.

19. A pharmaceutical composition for reducing sodium nitroprusside-induced toxic effects comprising:
   a. alpha-ketoglutaric acid;
   b. a physiological saline solution;
   c. said saline solution being about 0.9 percent sodium chloride;
   d. sodium thiosulfate; and
   e. a physiological pH-modifying substance in an amount effective to adjust the pH to about 7.4, wherein said alpha-ketoglutaric acid is present in an amount sufficient to deliver a dosage of about 0.1 g/kg to about 2.0 g/kg of body weight and said sodium thiosulfate is present in an amount of about 10 grams total dose.

* * * * *